United States Patent [19]

De Luca et al.

[11] Patent Number: 5,002,963

[45] Date of Patent: Mar. 26, 1991

[54] 3-INDOLEPYRUVIC ACID DERIVATIVES AND PHARMACEUTICAL USE THEREOF

[76] Inventors: Giovanna De Luca, 124 Via Ugo de Carolis; Giovanni Di Stazio, 221 Via Clivo di Cinna, both of I-00136 Roma RM; Andrea Margonelli, 65 Via G. Massaia, I-00154 Roma RM; Mario Materazzi, 10 Via Delleani, I-00155 Roma RM; Vincenzo Politi, 77 Via Albano, I-00179 Roma RM, all of Italy

[21] Appl. No.: 327,804

[22] PCT Filed: Jun. 1, 1988

[86] PCT No.: PCT/IT88/00041

§ 371 Date: Feb. 3, 1989

§ 102(e) Date: Feb. 3, 1989

[87] PCT Pub. No.: WO88/09789

PCT Pub. Date: Dec. 15, 1988

[30] Foreign Application Priority Data

Jun. 3, 1987 [IT] Italy ............................. 48014 A/87

[51] Int. Cl.$^5$ ................. C07D 209/18; A61K 31/405
[52] U.S. Cl. ..................................... 514/419; 548/494
[58] Field of Search ........................ 548/494; 514/419

[56] References Cited

FOREIGN PATENT DOCUMENTS

| 0046291 | 2/1982 | European Pat. Off. . |
| 0046953 | 10/1982 | European Pat. Off. . |
| 0048159 | 12/1982 | European Pat. Off. . |
| 1550993 | 8/1979 | United Kingdom . |

OTHER PUBLICATIONS

Chemical Abstracts, vol. 91:21026g.
Chemical Abstracts, vol. 75:05992w.

Primary Examiner—David B. Springer

[57] ABSTRACT

The present invention is directed to 3-indolepyruvic acid derivatives, compositions and methods of treating central nervous system disturbances due to the presence of an excessive amount of excitatory amino acids.

8 Claims, No Drawings

3-INDOLEPYRUVIC ACID DERIVATIVES AND PHARMACEUTICAL USE THEREOF

DESCRIPTION

The present invention relates to novel compounds which are derivatives, in the form of salts, esters and amides, of 3-indolepyruvic acid.

The present invention further relates to the use of 3-indolepyruvic acid, and the above mentioned derivatives thereof, as pharmaceutically active agents for the treatment of disturbances of the central nervous system produced in the brain by the presence of a great amount of superoxide anions or free radicals. Representatives of such disturbances are epilepsy, cerebral ischemia, ictus and Alzheimer's disease.

It has been shown that pharmaceutical administration of the compounds according to the invention produces at the brain level an increase of kynurenic acid, which has been recognised as a natural antagonist of the excitatory aminoacids.

REFERENCES TO THE PRIOR ART 3-indolepyruvic acid is a known compound.

In published European Patent Application No. 106813, corresponding to U.S. Pat. No. 4551471, a process for the enzymatic synthesis of 3-indolepyruvic acid is described, which uses aspartate aminotransferase as an enzyme.

In published European Application No. 0227787 a process for the chemical synthesis of 3-indolepyruvic acid is described, which uses a coupling reaction starting from L-tryptophan.

Moreover, it has been known for several years that tryptophan derivatives can interact in mammals with the receptors of so-called "excitatory aminoacids", namely glutamate, N-methyl-aspartate, ibotenic acid, kainic acid, and so on.

In particular it has been observed that quinolinic acid and kynurenine are powerful agonists of excitatory aminoacids present in the central nervous system of mammals (as an example see: Science 219, 316-8, 1983; Neuropharmacology 23, 333-7, 1984) and they can lead to a rapid neuronal decay similar to that observed in epilepsy and Huntington's Chorea (TIPS 1984, page 215).

The clinical importance of the excitatory aminoacids has become of considerable interest, such as to induce the organization of periodical symposiums for up-dating, such as the one held in London on the 13th and 14th April 1987 ("Excitatory aminoacids in health and disease") and the publication of full monographic editions in scientific magazines (see TINS, Volume 10, No. 7, 1987). According to the most recent views, the inhibitors of excitatory aminoacids can be used for blocking tremor and spasticity, epilepsy, neurodegenerative disorders, cerebral ischemia, psychosis, and the consequences of cerebral ictus (Scrip 1198, 27, 1987).

It has recently been discovered that a further derivative of tryptophan, namely kynurenic acid, is a powerful inhibitor of the excitatory effects manifested by quinolinic acid, N-methyl-D-aspartate and other aminoacids (J. Pharmacol. Exptl. Ther. 236, 293-9, 1986) and it could therefore hinder the neuronal decay in the brain produced by the above mentioned compounds during epileptic attacks, ictus, cerebral ischemia and more generally in neuronal alteration effects occurring during aging.

However, it is not possible to obtain an increase of kynurenic acid at the brain level by means of the administration of kynurenic acid itself, in that the blood-brain barrier prevents the compound from reaching the brain from the outside. Consequently it cannot be usefully administered either orally or via normal injection, to increase the cerebral level of kynurenic acid. It is known, moreover, from the prior art that kynurenic acid is an endogenous compound. It is originated in very small amounts from food tryptophan. However, not even tryptophan can be administered as a drug for this use, in that it is also transformed into kynurenines which have an action which antagonizes that of kynurenic acid.

It has been shown previously (published European Application No. 106813) that 3-indolepyruvic acid is a privileged precursor of cerebral serotonin and, as such, it could be used pharmacologically in all the diseases characterized by a lack of such an endogenous amine.

SUMMARY OF THE INVENTION

It has now been surprisingly found that 3-indolepyruvic acid, as well as many simple derivatives thereof, can be easily transformed "in vivo" in mammals into kynurenic acid and that the cerebral level of this acid can be substantially increased.

In fact it is surprising and it is an extremely useful result, in accordance with the hereinbefore exposed considerations, that the level of kynurenic acid in the brain can be increased by administration of 3-indolepyruvic acid or a compound according to the invention.

On the basis of pharmacological tests which will be hereinafter reported, which evidence an increase of kynurenic acid at the brain level following an administration of the compounds according to the invention, an explanation is given hereinbelow of the possible mechanism of action.

The fact that 3-indolepyruvic acid is easily transformed into kynurenic acid in all the organs subjected to our tests, whereas other derivatives of the kynurenine class are absent, suggests that the ketoacid undergoes he following transformations in the mammal organism:

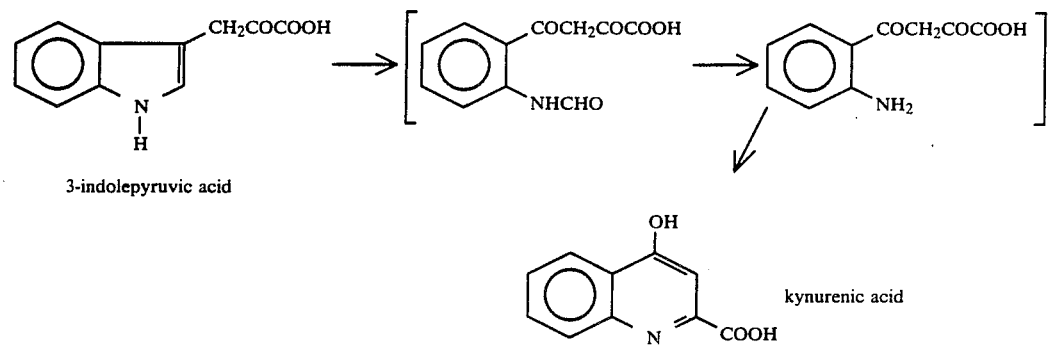

3-indolepyruvic acid kynurenic acid

The opening of the indole ring of 3-indolepyruvic acid could be produced through indoleamine-dioxygenase enzyme, which is known to be present in all mammal tissues and to act only in the presence of superoxide anions (see for example: J.Biol.Chem. 250, 5960-6, 1975). However, a direct opening of the ring even in the absence of enzymes cannot be excluded, as it is known that the superoxide anions and the free radicals are extremely active compounds and the formation of kynurenic acid from 3-indolepyruvic acid has also been ascertained in "in vitro" systems without any presence of mammal tissues (see Test No. 1 hereinafter reported).

As it is generally proved that the superoxide anions and the free radicals are involved in the raising of a plurality of situations of neuronal decay (see "Free radicals in medicine and biology", Acta Physiol. Scand. suppl. 492, 1980), 3-indolepyruvic acid and the derivatives thereof appear to be selective agents for increasing the levels of kynurenic acid in the brain, mainly in situations of cerebral disturbance, and consequently they can be used as drugs in pathologies such as epilepsy, ictus, cerebral ischemia and dementia senilis of the Alzheimer's type.

A process for the production of 3-indolepyruvic acid can be effected starting from L-tryptophan, comprising reacting L-tryptophan with L-aminoacid oxydase enzyme in an oxygen containing aqueous medium at a pH of about 7,5.

Object of the invention are novel derivatives of 3-indolepyruvic acid of formula

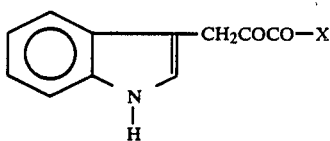

in which X is —OR, —NHR, —NR₂, or

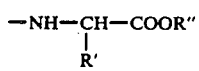

wherein

R is methyl, ethyl, propyl, isopropyl, butyl, tert.butyl, cyclohexyl, or benzyl, R' is a group which, together with the group

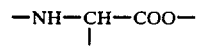

forms an aminoacid radical, and R" is H, or methyl, ethyl, propyl, isopropyl, butyl, tert.butyl, cyclohexyl, or benzyl, and the alkali and earth-alkali metal salts of 3-indolepyruvic acid.

A further object of the invention are pharmaceutical formulations containing the above mentioned novel compounds for the treatment of disturbances of the central nervous system produced by the presence in the brain of a large amount of superoxide anions or free radicals, and the use of 3-indolepyruvic acid and the derivatives thereof of formula 1, for the manufacture of medicaments for the above mentioned therapeutical indication.

Description of the process for the production of 3-indolepyruvic acid 3-indolepyruvic acid can be prepared starting from L-tryptophane, taking advantage of a new method of enzymatic synthesis. In fact the aminoacid is reacted with L-aminoacid oxydase, an enzyme which is present in a large amount in a number of snake venoms, in a continuously oxygenated aqueous medium. 3-indolepyruvic acid is formed according to the following reaction:

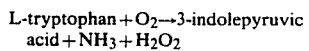

To avoid the degradation by $H_2O_2$ of the ketoacid formed, catalase, an enzyme which transforms $H_2O_2$ into $H_2O$ and $O_2$, is also added to the solution.

A considerable amount of 3-indolepyruvic acid can be obtained in a continuous flow reactor comprising a first column filled with resin to which a suitable amount of L-aminoacid oxydase and catalase enzymes have been linked.

L-aminoacid oxydase enzyme can be obtained from the venom of several snake species, such as: Ankistrodon, Bitis, Crotalus, Dendroaspis, Naja, Pseudechis, Trimeresurus, viper, and the like.

Catalase can be obtained from cattle liver, for example.

It has been shown that a plurality of resins are able to link the enzymes, in such a way as not to affect their catalytic activity. Among them, particularly useful are Eupergit C type resin (produced by Rohm Pharma), Aminoaril CPG (produced by Pearce), Michroprep silica (produced by E. Merck) and sodium alginate coated with quaternized polyethylene-imine.

In the second column an ion exchange resin is charged (such as Amberlite X AD-4), able to hold 3-indolepyruvic acid formed and allow the passage of tryptophan to be recycled.

The system was activated by two peristaltic pumps of the same flow rate, connected to the first column and to the reactant supply, consisting of a buffered L-tryptophan solution (such as phosphate buffer with a pH from 7 to 8).

Hereinafter an example of preparation of 3-indolepyruvic acid is described.

500 mg L-aminoacid oxydase enzyme from venom of Crotalus Atrox were dissolved into phosphate buffer 1 M pH 7,5.

6 g Eupergit C resin were added under light stirring and left standing for 24 hours at room temperature. At the same time 10 mg of catalase from cattle liver were added to 10 ml of 1 M phosphate buffer pH 7,5.

3 g Eupergit C resin were then added under light stirring and left standing for 24 hours at room temperature. The resins were united in a porous filter and the solution was eluted by gravity. After washing with 300 ml of 0,1 M phosphate buffer pH 7,5, the resin was packed into a first column. A second column was charged with 5 g Amberlite X AD-4 resin, previously adjusted with 0,1 M phosphate buffer pH 7,5. 500 mg L-tryptophan in 100 ml of 0,1 M phosphate buffer pH 7,5 were added in the solution supply. The flow rate was set at 1 ml/minute. After 22 hours the second column was cut off and the solution was eluted with methanol.

The 3-indolepyruvic acid thus obtained was dried and weighed (about 200 mg).

Preparation of the derivatives of 3-indolepyruvic acid

The 3-indolepyruvic acid derivatives were synthesized with the aim of enabling the compounds to pass more easily through the blood-brain barrier and consequently to increase the levels of kynurenic acid formed in the central nervous system.

For this synthesis four routes were essentially followed:

(a) the salts were obtained by the alcoholates of the corresponding metals in anhydrous ether;

(b) methyl ester of 3-indolepyruvic acid was produced by reacting the acid with diazomethane;

(c) methyl ester and other esters were produced by reacting the carboxylic ion with alkyl halides, with corresponding nucleophylic substitution of the halogen. As the acid is highly instable, a salification reaction was initally effected with DBU (1,8-diazabicyclo-|5.4.0|-undec-7-ene), which forms a complex with a large charge displacement. This complex, which is strongly nucleophylic and a weak base, can attack primary, secondary, tertiary alkyl and benzyl halides, without giving rise to simultaneous elimination reactions. In this manner methyl, ethyl, isopropyl, tert.butyl, benzyl esters were synthesized and in a similar manner propyl, butyl, cyclohexyl esters and the like can be synthesized;

(d) amide type compounds were obtained by a reaction activating the carboxyl group of 3-indolepyruvic acid by means of a carbodiimide, in the presence of hydroxybenzotriazole, with formation of the corresponding activated ester. This is attacked by an amine group with formation of the corresponding amide bond (when an amine was dealt with) or a peptide bond (when a protected aminoacid was dealt with).

Hereinafter some examples of preparation for the 3-indolepyruvic acid derivatives are described.

EXAMPLE 1

Preparation of the Mg salt of 3-indolepyruvic acid.

The compound was prepared by reacting the ketoacid with magnesium oxide in an anhydrous ether medium:

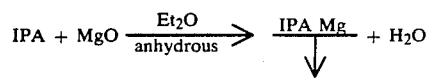

An anhydrous ether solution of 3-indolepyruvic acid (IPA) (200 mg) is additioned with 40 mg MgO under stirring and argon environment, at 20°-25° C. The suspension was stirred for one night. A large amount of flocculent water soluble precipitate was recovered, which was carefully washed with Et$_2$O. The precipitate was dried under vacuum for one night. The conversion into salt was about 90%. This salt shows a 215° C. melting point with decomposition.

EXAMPLE 2

Sodium, potassium, calcium and barium 3-indolepyruvates are produced in the same manner as described in Example 1.

EXAMPLE 3

Preparation of 3-indolepyruvic acid methyl ester.

1,0 g of 3-indolepyruvic acid were suspended into 50 ml anhydrous benzene under argon atmosphere.

1,5 ml DBU were added at room temperature, under brisk stirring. Heating was then started for refluxing benzene.

Almost immediately the yellow suspension changes into a dark yellow rubbery solid, which makes stirring difficult. At a temperature of about 50° to 60° C. 1,0 ml CH$_3$I diluted in 5 ml anhydrous benzene were added. On refluxing benzene, it was noted that the rubbery solid was transformed into a brown-red compound.

After one night refluxing under argon atmosphere, the benzene solution was decanted and the reddish solid was taken with CH$_2$Cl$_2$ until dissolved. The organic solutions were united and the precipitate was filtered off. The organic solution was washed successively with 5% solution NaHCO$_3$ (10×50 ml), saturated NaCl solution up to neutrality, 5% solution of KHSO$_4$ (10×50 ml) and saturated NaCl solution up to neutrality. After leaving for one night on anhydrous Na$_2$SO$_4$, this was filtered off and the residue was purified by flash chromatography on silica gel (eluent CH$_2$Cl$_2$ 90/acetone 10), thus obtaining a lightly yellow chromatographically pure solid (one spot on TLC and one peak in HPLC).

The structure was confirmed by IR and NMR spectrometry. The yield was about 60%.

EXAMPLE 4

Preparation of 3-indolepyruvic acid ethyl ester.

Following the same method as previously described, 1,0 g 3-indole-pyruvic acid were reacted with 1,5 ml DBU and 790 microliters ethylbromide. In this case the benzene solution appeared red orange. After flash chromatography purification the ethyl ester was obtained with a yield of about 70%.

EXAMPLE 5

Preparation of 3-indolepyruvic acid benzyl ester.

Following the same method as previously used, 1,0 g 3-indolepyruvic acid were reacted with 1,5 ml DBU and 850 microliters benzylchloride. The benzene solution before the extractions appeared red orange. Flash chromatography purification showed a 65% yield of benzyl ester.

EXAMPLE 6

In a similar manner as described in the preceding examples, the propyl, isopropyl, butyl, tert.butyl and cyclohexyl esters are prepared.

EXAMPLE 7

Preparation of N,N-dimethyl 3-indolepyruvamide.

A solution of 500 mg 3-indolepyruvic acid in 25 ml anhydrous tetrahydrofuran on an ice-salt bath, under argon atmosphere and under stirring was additioned in swift succession with: 400 mg hydroxybenzotriazole (HOBt) and 570 mg 1-(3-dimethylaminopropyl)-3-ethylcarbimdie.HCl (EDC.HCl). After dissolving and still maintaining the ice-salt bath, 240 mg dimethylamine.HCl were added dissolved in 10 ml anhydrous tetrahydrofuran and 325 microliters 4-methylmorpholine (NMM). The yellowish gold solution was maintained under stirring for one night, leaving the bath temperature to rise up to room temperature. The volume was then tripled adding $CH_2Cl_2$ and the organic solution was washed in sequence with 5% $NaHCO_3$ (10×25 ml), saturated NaCl solution (3×25 ml), 5% $KHSO_4$ (10×25 ml) and saturated NaCl solution up to neutrality. After standing for one night on anhydrous $Na_2SO_4$, this was filtered off, the mixture was purified by flash chromatography (silica gel, eluent $CH_2Cl_2$ 25/n-propanol 1,5).

A strongly hygroscopic solid was obtained which showed itself to be pure on TLC and on HPLC. The amide was characterized by IR and NMR spectra (yield about 35%).

EXAMPLE 8

Preparation of N-cyclohexyl 3-indolepyruvamide.

The same method as described in Example 7 was followed for the preparation of N,N-dimethylamide. 500 mg 3-indolepyruvic acid were reacted with 400 ml HOBt and 570 ml EDC.HCl. 340 microliters of freshly distilled cyclohexylamine and 325 microliters NMM were added to the solution, which was reacted for 5 hours.

After flash chromatography purification, a yield of about 50% was detected.

EXAMPLE 9

Preparation of N-benzyl 3-indolepyrivamide.

Following the same method as previously described in Example 7, 500 mg 3-indolepyruvic acid were reacted with 400 mg HOBt and 570 mg EDC.HCl. 425 mg benzylamine and 325 microliters NMM were then added. After reacting for one night, it was purified by flash chromatography.

The final yield appears to be about 55%.

EXAMPLE 10

Following the same method as described in Examples 7 to 9, N,N-diethyl, N,N-dipropyl, N,N-dibutyl, N-methyl, N-ethyl, N-propyl, N-isopropyl, N-butyl, N-tert.butyl 3-indolepyruvoamide are produced.

Pseudo-dipeptides have been prepared by reaction of 3-indolepyruvic acid (IPA) and methyl esters of aminoacids.

EXAMPLE 11

Preparation of IPA-L-ALA-OMe.

400 mg HOBt and 570 mg EDC.HCl were added in a swift sequence to a solution of 500 mg 3-indolepyruvic acid in 30 ml anhydrous tetrahydrofuran under stirring, on an ice-salt bath and under argon atmosphere. After dissolving and maintaining the ice-salt bath, a cold solution of 415 mg L-alanine methylester.HCl in 10 ml anhydrous tetrahydrofuran and 325 microliters NMM was added. The yellowish solution was stirred for three hours leaving the temperature to rise to room temperature. Then the volume was tripled with $CH_2Cl_2$ and the reaction mixture was successively treated with 5% $NaHCO_3$ (10×20 ml), saturated NaCl solution (3×50 ml), 5% $KHSO_4$ (10×20 ml) and saturated NaCl solution up to neutrality. The yellowish solution was left standing for one night on anhydrous $Na_2SO_4$, then this was filtered off and the pseudo-dipeptide was purified by flash chromatography.

A hydroscopic yellowish solid was obtained, which appeared pure on TLC and in HPLC. The structure was confirmed by IR and NMR spectra. Yield was 40%.

Following the same method the compound IPA-D-ALA-OMe was prepared, obviously starting from D-alanine.

Both the esters were then unblocked to obtain the free acids.

EXAMPLE 12

Preparation of IPA-L-PHE-OMe, IPA-D-PHE-OMe and the corresponding free acids.

By the same method as previously described, 500 mg 3-indolepyruvic acid were reacted with 400 mg HOBt and 570 mg EDC.HCl. 640 mg phenylalanine methylester hydrochloride (L or D) and 325 microliters NMM were then added. After reacting for five hours and purifying, hygroscopic yellowish solids were recovered with a yield of about 55%.

EXAMPLE 13

Preparation of IPA-L-TYR-OMe, IPA-D-TYR-OMe and the corresponding free acids.

By using the same method as previously described, 500 mg of 3-indolepyruvic acid were reacted with 400 mg HOBt and 570 mg EDC.HCl. 690 mg tyrosine methylester (L or D) and 325 microliters NMM were added. After reacting for five hours and purifying, hygroscopic yellowish-gold solids were recovered with a yield of 65%.

EXAMPLE 14

Preparation of IPA-L-PRO-OMe, IPA-D-PRO-OMe and the corresponding free acids.

Following the same method as previously described, 500 mg 3-indolepyruvic acid were reacted with 400 mg HOBt and 570 mg EDC.HCl. 370 mg proline methylester hydrochloride (L or D) and 270 microliters NMM were added. After reacting for one night and purifying, hygroscopic yellowish solids were recovered with a yield of 40%.

EXAMPLE 15

Following the same method as described in Examples 10 to 14, the other pseudo-dipeptides are obtained by reacting 3-indolepyruvic acid with the corresponding aminoacid methylester.

Pharmacological tests

Pharmacological tests have been carried out to evaluate the levels and the activity of kynurenic acid in various animal organs.

For the measurement of such levels after administration of 3-indolepyruvic acid or a derivative thereof, a system was set up based on ultraviolet detection of the compounds separated by high pressure liquid chromatography.

Briefly, after sacrific of the animal, some of the principal organs were taken and homogenized with alkaline ethanol. Proteins and cell remains were removed by centrifugation, whilst the over natant was adsorbed on Bio-Rad AG 1×8 resin. After washing with water it was eluted with formic acid. It was then passed on Bio-Rad AG 50W-×8 resin, eluted with 3% ammonia, dried and retaken with a small amount of water.

The sample thus obtained was injected into a Waters apparatus for high pressure liquid chromatography, using a C18 10 micron column and eluting with 0,02 m citric acid containing 10% of methanol. The kynurenic acid levels were extrapolated by the calibration line of the acid and reading at 234 nm.

The tests hereinafter reported have the object of illustrating the effect of administration of IPA and the derivatives thereof of formula 1, on the production of kynurenic acid in the brain. The tests also show that the agent producing such an effect is IPA, rather than tryptophan.

It is well known in fact, as mentioned hereinbefore, that tryptophan (briefly TRP) is transformed into kynurenines within the peripheral tissues and a doubt could be raised that these kynurenines could be responsible for the production of kynurenic acid in the brain. This however is not the case, as the following test show. The tests confirm that only an administration of IPA causes the level of kynurenic acid in the brain to increase substantially.

Test 1

Transformation of 3-indolepyruvic acid into kynurenic acid "in vitro", within a non enzymatic system.

When 3-indole pyruvic acid or a derivative thereof of formula 1 is incubated in a slightly acid solution (HCl 0,1 M), in the presence of oxidising agents ($O_2$) and light, in time the formation of small amounts of kynurenic acid is observed. Particularly starting from 2 mg 3-indolepyruvic acid, 0,5 micrograms are obtained after 2 hours and 0,7 micrograms after 4 hours.

This test shows that 3-indolepyruvic acid is transformed, even without enzymes, into kynurenic acid, even "in vitro".

Test 2

Transformation of 3-indolepyruvic acid into kynurenic acid in tissue homogenates.

Male rats fasting for 16 hours were sacrificed and their organs were taken and homogenized in 5 volumes of 0,05 M phosphate buffer pH 7,4+0,14 M KCl.

Small amounts of homogenate (0,8 ml) were additioned with various amounts of 3-indolepyruvic acid or the derivatives thereof, dissolved into a buffer solution, and with a system for the production of free radicals, consisting of ascorbic acid (final $10^{-5}$ M), $FeCl_3$ (final $10^{-6}$ M) and $H_2O_2$ (final $10^{-4}$ M). It was stirred at 37° C., then the reaction was blocked. The following results were obtained.

TABLE 1

| Kidney homogenate Amount of kynurenic acid formed | | | | |
| --- | --- | --- | --- | --- |
| | | 30' | 60' | 120' |
| 3-indolepyruvic acid | final 0.8 mg | 160 ng | 190 ng | 208 ng |
| 3-indolepyruvic acid | final 1.6 mg | 232 ng | 280 ng | 315 ng |
| 3-indolepyruvic acid | final 4 mg | 185 ng | 221 ng | 270 ng |
| Tryptophan | final 1.6 mg | 55 ng | 82 ng | 111 ng |

TABLE 2

| Brain homogenate Amount of kynurenic acid formed | | | | |
| --- | --- | --- | --- | --- |
| | | 30' | 60' | 120' |
| 3-indolepyruvic acid | 1.6 mg | 165 ng | 280 ng | 380 ng |
| Tryptophan | 1.6 mg | 0 | 0 | 0 |
| IPA-Methylester | | 48 ng | 65 ng | 83 ng |
| IPE-TYR-Ome | | 44 ng | 48 ng | 79 ng |
| IPE-PHE-Ome | | 75 ng | 82 ng | 92 ng |

IPA = 3-indolepyruvic acid
IPA-TYR-Ome = 3-indolepyruvic acid tyrosine methylester
IPA-PHE-Ome = 3-indolepyruvic acid phenylalanine methylester The results show that kynurenic acid is formed in time when 3-indolepyruvic acid is incubated with homogenates of various organs.

Tryptophan in the brain is never transformed into kynurenic acid, as shown in Table 2, and this evidences that the transformation into kynurenic acid only occurs directly from IPA ketoacid.

In the kidney, where kynurenine transaminase is present, it is possible that kynurenic acid is also formed from kynurenine. It is known, however, that said kynurenic acid cannot reach the brain, in that this is hindered by the blood-brain barrier.

Moreover, Table 2 shows that the derivatives of IPA are also able to produce kynurenic acid when incubated in brain homogenate.

Resuming, this test shows that IPA is able to transform into kynurenic acid in the brain, whereas tryptophan cannot.

Test 3

Effect on the content of kynurenic acid after administration of IPA in rat.

Male rats were treated with saline solution (controls) or with various doses of IPA, which was injected 3 hours before sacrifice. Each lot comprised 10 animals.

The results are reported in picomoles/g of tissue (or ml of blood)±standard error.

TABLE 3

| | Liver | Blood | Brain |
| --- | --- | --- | --- |
| Saline | 121 ± 5 | 25 ± 3 | 18 ± 2 |
| IPA - 100mg/Kg i.p. | 240 ± 20 | 62 ± 3 | 24 ± 1 |
| IPA - 100 mg/Kg per os | 275 ± 25 | 87 ± 8 | 28 ± 2 |
| IPA - 250 mg.Kg i.p. | 547 ± 35 | 164 ± 10 | 32 ± 3 |
| IPA - 250 mg/Kg per os | 485 ± 40 | 120 ± 12 | 38 ± 3 |
| IPA - 500 mg.Kg i.p. | 2860 ± 300 | 442 ± 20 | 110 ± 10 |

The results show that administration of IPA produces an increase in the levels of kynurenic acid in the tissues under test. Such an increase is dose-dependent. This fact is particularly relevant in the brain, where, for a 500 mg/Kg dose of IPA, values of kynurenic acid six times higher than the controls are obtained.

This test shows that an administration of IPA causes the level of kynurenic acid in the brain to increase to an extent depending on the dose. It is to be noted that, as previously illustrated, an administration of tryptophan does not produce such an effect.

Test 4

Effects on the content of tryptophan and kynurenic acid in the brain of rats, by treatment with IPA or tryptophan.

Male rats were treated with saline solution (controls), IPA or tryptophan i.p. one hour before sacrifice. Each lot was of six animals.

The reported values are in picomoles/g for kynurenic acid and picomoles/mg for tryptophan.

TABLE 4

|  | Kynurenic acid | Tryptophan | KYN/TRP × 10³ |
|---|---|---|---|
| Saline | 18 ± 2 | 21.3 ± 3 | 0.86 |
| IPA 250 mg.Kg | 47 ± 5 | 124 ± 10 | 0.40 |
| TRP 250 mg/Kg | 35 ± 3 | 206 ± 15 | 0.16 |

The results of this test show that in the brain, kynurenic acid is formed preferably by direct opening of the indole ring of IPA, rather than through the kynurenins.

IPA consequently can be considered as a selective precursor of cerebral kynurenic acid.

In fact, as in test No. 2 it was shown that TRP does not transform into kynurenic acid in the brain, the presence of kynurenic acid due to administration of TRP should be due to transformation into kynurenic acid of kynurenines coming from peripheral organs.

On the other hand, the ratio of the content of kynurenic acid to tryptophan excludes the same pathway for 3-indolepyruvic acid.

This proved that 3-indolepyruvic acid transforms directly into kynurenic acid in the brain.

Test 5

Time course of the kynurenic acid levels after administration of IPA.

Male rats, in lots of five animals each, were treated i.p. with 250 mg/Kg IPA and were sacrificed at different times, evaluating the levels of kynurenic acid present in various organs.

The results are reported in picomoles/g±standard error.

TABLE 5

|  | Control | 1 hour | 2 hours | 3 hours | 4 hours |
|---|---|---|---|---|---|
| Brain | 20 ± 2 | 39 ± 4 | 32 ± 3 | 38 ± 4 | 28 ± 3 |
| Liver | 80 ± 10 | 827 ± 50 | 464 ± 40 | 235 ± 5 | 122 ± 10 |
| Kidney | 262 ± 25 | 2593 ± 250 | 2395 ± 200 | 1480 ± 150 | 1200 ± 150 |
| Heart | 67 ± 7 | 181 ± 18 | 177 ± 20 | 104 ± 12 | 100 ± 11 |

The results show a high increase of kynurenic acid in all the organs under test (maximum in kidney). The levels remain high even after 4 hours from administration.

Test 6

Effect of administration of IPA or derivatives thereof on audiogenic convulsions in DBA2 mice.

To evaluate whether an increase in kynurenic acid in the brain after administration of IPA could have a protective action on neurons stressed by excitatory aminoacids, the experimental pattern of inducing convulsions in a particular strain of mice (DBA2) by selected sound stimulations was followed. In such pattern kynurenic acid is protective against convulsions.

The substances were injected intravenously one hour before the test. Then the number of animals showing tonic convulsions was measured.

TABLE 6

|  | Animals with convulsions | % |
|---|---|---|
| Controls | 9/14 | 65% |
| IPA 200 mg/Kg | 4/12 | 33% |
| Tryptophan 200 mg/Kg | 8/10 | 80% |
| $Mg^{++}$ IPA salt | 4/14 | 29% |

The results show a good protective action by IPA and its $Mg^{++}$ salt against tonic convulsions induced by sound stimulations on DBA2 mice. On the contrary, tryptophan showed no effective action.

Test 7

Action of administration of IPA on NMDA induced convulsions.

N-methyl-D-aspartic acid (NMDA) is a compound having a powerful neurotoxic effect, due to activation of specific receptors of the excitatory aminoacids. As it is well known that kynurenic acid protects against the toxicity due to NMDA, the action of IPA, as precursor of kynurenic acid, was evaluated against the toxicity of such compound.

Mice of Albino Swiss strain were treated with saline (controls) or with IPA (1 g/Kg i.p.) one hour before receiving a toxic dose of NMDA (154 mg/Kg i.p.).

TABLE 7

|  | Tonic convulsions | Deaths |
|---|---|---|
| Controls | 9/10 | 8/10 |
| Treated | 5/9 | 3/9 |

From the above results it can be assessed that IPA is able to protect mice against both convulsions and death induced by NMDA.

It follows that 3-indolepyruvic acid and the above described derivatives thereof, can be used for the treatment of human and animal diseases due to a lack of kynurenic acid at the brain level and more generally for the treatment of disturbances of the central nervous system produced by the excitatory aminoacids.

The administration can be made by means of pharmaceutical compositions containing the active substance in a dose of about 2 to 20 mg/Kg body weight for a "per os" administration, and in a dose of about 1 to 10 mg/Kg body weight for a parenteral administration.

For the oral, parenteral or rectal administration the usual pharmaceutical forms can be used, such as pills, capsules, solutions, suspensions, injections, suppositories, in association with pharmaceutically acceptable carriers or diluents and excipients.

We claim:

1. A 3-indolepyruvic acid derivative having the formula

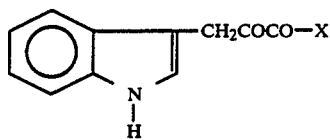

wherein X is

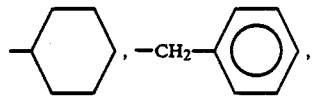

and wherein R is selected from methyl, ethyl, propyl, isopropyl, butyl, tert.butyl, cyclohexyl or benzyl; or a pharmaceutically acceptable salt thereof.

2. A pharmaceutical composition which comprises an effective amount of the compound according to claim 1; and a pharmaceutically acceptable carrier or diluent.

3. The composition according to claim 1, wherein the effective amount is sufficient to treat central nervous system disturbances due to the presence of an excessive amount of excitatory amino acids.

4. A method for the treatment of central nervous system disturbances due to the presence of an excessive amount of excitatory amino acids which comprises administering to said mammal in need thereof an effective amount of the compound having the formula

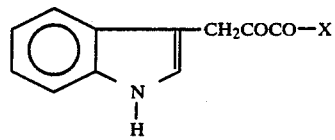

in which X is —OH, —OR, —NHR, —NH$_2$, or

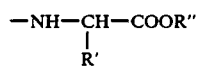

wherein R is methyl, ethyl, propyl, isopropyl, butyl, tert.butyl, cyclohexyl or benzyl, or a pharmaceutically acceptable salt thereof.

5. The method according to claim 4 wherein said disturbance is epilepsy.

6. The method according to claim 4 wherein said disturbance is cerebral ischemia.

7. The method according to claim 4 wherein said disturbance is ictus.

8. The method according to claim 4 wherein said disturbance is Alzheimer's Disease.

* * * * *